(12) United States Patent
Farsoni et al.

(10) Patent No.: US 12,102,461 B2
(45) Date of Patent: Oct. 1, 2024

(54) INTRAOPERATIVE RADIATION PROBE SYSTEM WITH RADIATION-ORIENTATION MAPPING

(71) Applicants: Abdollah T. Farsoni, Laguna Niguel, CA (US); Shahriar Tavakoli, Thornhill (CA)

(72) Inventors: Abdollah T. Farsoni, Laguna Niguel, CA (US); Shahriar Tavakoli, Thornhill (CA)

( * ) Notice: Subject to any disclaimer, the term of this patent is extended or adjusted under 35 U.S.C. 154(b) by 118 days.

(21) Appl. No.: 17/993,184

(22) Filed: Nov. 23, 2022

(65) Prior Publication Data
US 2024/0164732 A1    May 23, 2024

(51) Int. Cl.
*A61B 6/46*  (2024.01)
*A61B 6/00*  (2024.01)
*A61B 6/06*  (2006.01)

(52) U.S. Cl.
CPC .............. *A61B 6/463* (2013.01); *A61B 6/06* (2013.01); *A61B 6/481* (2013.01); *A61B 6/563* (2013.01); *A61B 2562/0219* (2013.01)

(58) Field of Classification Search
CPC .......... A61B 6/463; A61B 6/06; A61B 6/481; A61B 6/563; A61B 2562/0219
See application file for complete search history.

(56) References Cited

U.S. PATENT DOCUMENTS

| | | | |
|---|---|---|---|
| 2014/0135616 A1* | 5/2014 | Stein .................... | A61B 17/92 600/424 |
| 2020/0237446 A1* | 7/2020 | Drain .................... | A61B 34/20 |
| 2022/0087624 A1* | 3/2022 | Quinlan ............... | A61B 6/5247 |

\* cited by examiner

*Primary Examiner* — Chao Sheng

(57) ABSTRACT

The present invention relates generally to cancer surgery through intraoperative radio-guided procedures such as localization of sentinel lymph nodes and tumors in patients with breast cancer and melanoma. More specifically, it relates to an intraoperative radiation probe system with a standalone orientation tracking capability to further guide the surgeon in identifying and locating radio-labeled organs in human body through radiation-orientation mapping.

4 Claims, 5 Drawing Sheets

INTRAOPERATIVE RADIATION PROBE SYSTEM WITH RADIATION-ORIENTATION MAPPING

CROSS-REFERENCE TO RELATED APPLICATIONS

Not Applicable.

BACKGROUND

An intraoperative radiation probe is a handheld medical device containing a radiation detector such as scintillation or semiconductor radiation detection technologies sensitive to ionizing radiations such as gamma-rays or beta particles, for intraoperative use following injection of a radiopharmaceutical, to locate radio-labeled organs in human body such as sentinel lymph nodes by their radioactivity. Radiation probes or gamma probes are also used for RSL (radioactive seed localization), to locate small and non-palpable breast lesions. The radiation probe may be collimated by a tungsten collimator to further restrict the field of detection.

A common application for intraoperative gamma probes is in sentinel lymph node biopsy (SLNB). A sentinel lymph node biopsy is a procedure in which the sentinel lymph node is identified using a gamma probe (following injection of a radionuclide such as Tc-99m), removed, and examined to determine whether cancer cells are present. It is used in people who have already been diagnosed with cancer. A negative SLNB result suggests that cancer has not yet spread to nearby lymph nodes or other organs. A positive SLNB result indicates that cancer is present in the sentinel lymph node and that it may have spread to other nearby lymph nodes (called regional lymph nodes) and, possibly, other organs. This information can help a surgeon determine the stage of the cancer (extent of the disease within the body) and develop an appropriate treatment plan.

In a typical SLNB procedure, the surgeon makes a small incision (about ½ inch) in the overlying skin where high radioactivity observed, then inserts the gamma probe into the opening to precisely locate and remove sentinel lymph nodes with the highest activities. Typically one to five sentinel lymph nodes may be removed during a SLNB procedure. To reduce the false negative rates, several clinical investigations with patients diagnosed with breast cancer have emphasized the importance of a meticulous intraoperative search for additional sentinel lymph node candidates with count-rates of at least 10% of the count-rates of the hottest nodes.

During the SLNB procedure and while the gamma probe is inside a small opening, the surgeon searches for additional sentinel lymph node candidates by changing the orientation of the gamma probe. For this, the surgeon pays attention to the count-rate changes either by looking at the count-rate values shown on a control unit or by listening to the audible signals. Changes in the count-rate versus instantaneous probe orientation in which the change has occurred are not recorded, therefore in many cases, the surgeon can only rely on his/her memory to locate multiple radio labeled organs such as sentinel lymph nodes.

Presently, most of commercialized radiation probes provide only radiation count-rates and accumulated counts. This information is either displayed by their values (Node Seeker 2000, IntraMedical Imaging, LLC) or by a graphical presentation on a control unit (Trunode, Hologic) or on the gamma probe itself (Gamma Finder III, W.O.M. World of Medicine GmbH). Audible signals, proportional to the count-rates, are also produced in these devices.

One system that is able to reconstruct a 3-dimensional distribution of gamma-ray count-rates based on gamma probe technology is Declipse®SPECT system manufactured by Surgiceye GMBH, Munich, Germany (Bluemel et al. 2016. "3D Scintigraphic Imaging and Navigation in Radioguided Surgery: Freehand SPECT Technology and Its Clinical Applications." Expert Review of Medical Devices, Volume 13, 2016—Issue 4; Wendler et al, 2010. "First demonstration of 3-D lymphatic mapping in breast cancer using freehand SPECT." Eur J Nucl Med Mol Imaging 2010-37(8)). As disclosed in U.S. Pat. No. 20090259123 A1 and U.S. Pat. No. 20130338490 A1, the Declipse®SPECT system uses fixed-position external infrared or other optical cameras, a gamma probe, and several infrared or other optical markers that should be attached on the gamma probe and the patient to track the position and orientation of the gamma probe relative to the patient during an intraoperative procedure. The system combines a gamma probe's radiation readings and navigation data from the infrared cameras to reconstruct a 3-dimensional distribution of gamma-ray count-rates in the patient's body. Comparing with other gamma probes in the market, this system is complex, bulky, much more expensive, and therefore imposes limited accessibility.

The U.S. Pat. No. 20060106306 A1 discloses a radiation probe technology for locating cancer cells in lymph nodes which utilizes a radiation detector operatively connected to an ultrasound probe for locating the position of radiation tagged tissue, particularly in sentinel lymph nodes followed by placement of a biopsy device.

The U.S. Pat. No. 6,643,538 B1 discloses a radiation probe technology in which a CCD camera is utilized with a radiation probe to generate a visual image containing radiation distribution in body or tissue.

One other example of the prior art in the context of the present invention is disclosed for example in U.S. patent Ser. No. 11/464,503 B2. This discloses a hand held medical navigation apparatus that includes a position sensitive radiation detector, an integrated tracking camera, and fiducial markers to determine the location of any signal of interest. The patent further discloses a method to fuse visual images captured by the camera with the distribution of nuclear emitting sources in the body as detected by the position sensitive radiation detector.

Some disclosed prior arts for intraoperative radiation probes with position and orientation tracking capability use overhead optical stereoscopic systems in conjunction with infrared reflective spheres or markers attached to the instruments and patient. Other devices use camera systems attached to the radiation probe to track the position and orientation of the probe with respect to the patient. The function of these devices often depends on one or more instruments remaining in the line-of-sight of the tracking camera to determine the correct position and orientation of the intraoperative radiation probes. Furthermore, these devices are complex, bulky, much more expensive, and therefore impose limited accessibility.

As such, there is a need in the art for simple but efficient intraoperative radiation probe systems that independently, without using a complex external orientation-tracking or navigation system, can record and display mapping information between the measured radiation count-rates and the instantaneous orientation of the radiation probe to assist the surgeon in identifying and locating radio-labeled organs during an intraoperative radio-guided procedure.

SUMMARY

Disclosed are the embodiments of an intraoperative radiation probe system with an integrated orientation-tracking technology that is able to generate radiation-orientation mapping images corresponding to the measured radiation count-rates and the instantaneous orientation of the radiation probe in space, without using a complex external orientation-tracking or navigation system. The radiation-orientation mapping image further guides the surgeon to efficiently identify and locate radio-labeled organs such as sentinel lymph nodes during an intraoperative sentinel lymph node biopsy (SLNB) procedure.

DETAILED DESCRIPTION

Disclosed herein is an intraoperative radiation probe system for intraoperative radio-guided surgery. The system is composed of a handheld radiation probe and a or a control unit with a display screen which is wirelessly connected to the handheld radiation probe and configured to run an application software for generating and displaying radiation-orientation mapping images.

The radiation probe is equipped with an orientation-tracking technology to track the orientation of the radiation probe and generate a radiation-orientation mapping image while is being used by the surgeon. The radiation-orientation mapping image further guides the surgeon to efficiently identify and locate radio-labeled organs such as sentinel lymph nodes during an intraoperative sentinel lymph node biopsy (SLNB) procedure.

Figure 1:
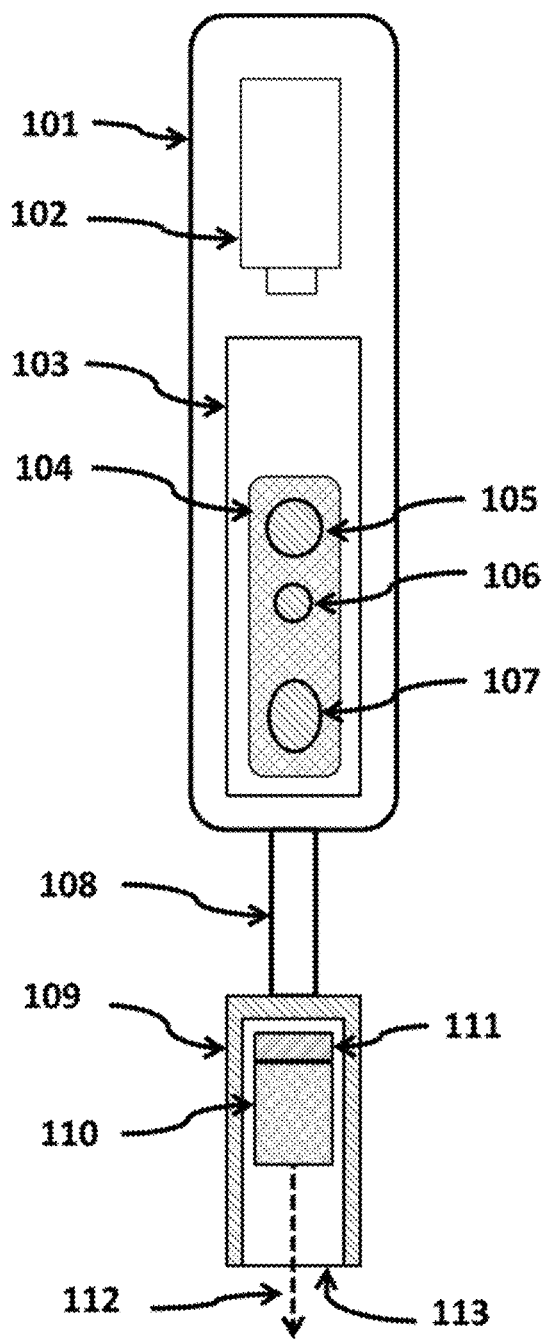
FIG. 1 shows an illustration of one embodiment of the intraoperative radiation probe.

In one embodiment, the radiation probe illustrated in FIG. 1 is composed of a plastic enclosure 101, a battery 102, a main electronics board 103, a user interface 104, a straight metallic arm 108, a tungsten collimator 109, a nuclear radiation detector 110, and a detector's electronics board 111.

In other embodiments, the radiation probe illustrated in FIG. 1 may have a bended metallic arm to provide a better access to desired detection locations. A straight metallic arm 108 in shown in FIG. 1.

The plastic enclosure 101 includes a battery cap (not shown in FIG. 1) for removing the battery when the battery 102 should be replaced. The main electronics board 103 includes electronics to process signals from the radiation detector as well as electronics to process orientation-tracking data from an inertial measurement unit. The main electronics board 103 also includes a wireless interface to exchange the collected data with a personal computer or a control unit wirelessly.

In a preferred embodiment, the user interface 104 is a membrane switch panel that is mounted on the external surface of the plastic enclosure 101 and is accessible by the user. The user interface 104 includes two push buttons 105 and 107 and a LED indicator 106. In a preferred embodiment, the push button 105 is used to power the probe and the push button (reset button) 107 is used to define a new reference orientation by the user. The LED indicator 106 may be used to notify the user about several operation status of the radiation probe such as wireless connection status and the battery level.

The radiation detector 110 and detector's electronics board 111 are assembled inside a tungsten collimator 109 to further restrict the field of detection. The tungsten collimator has an opening window 113 where radiations can enter the detector assembly and interact with the radiation detector 110. The tungsten collimator 109 is attached to the plastic enclosure by the metallic arm 108. Wires carrying radiation detector signals are routed through the arm 108. Arrow 112 indicates the orientation of the radiation probe in space along which maximum radiation detection efficiency can be achieved.

Figure 2:
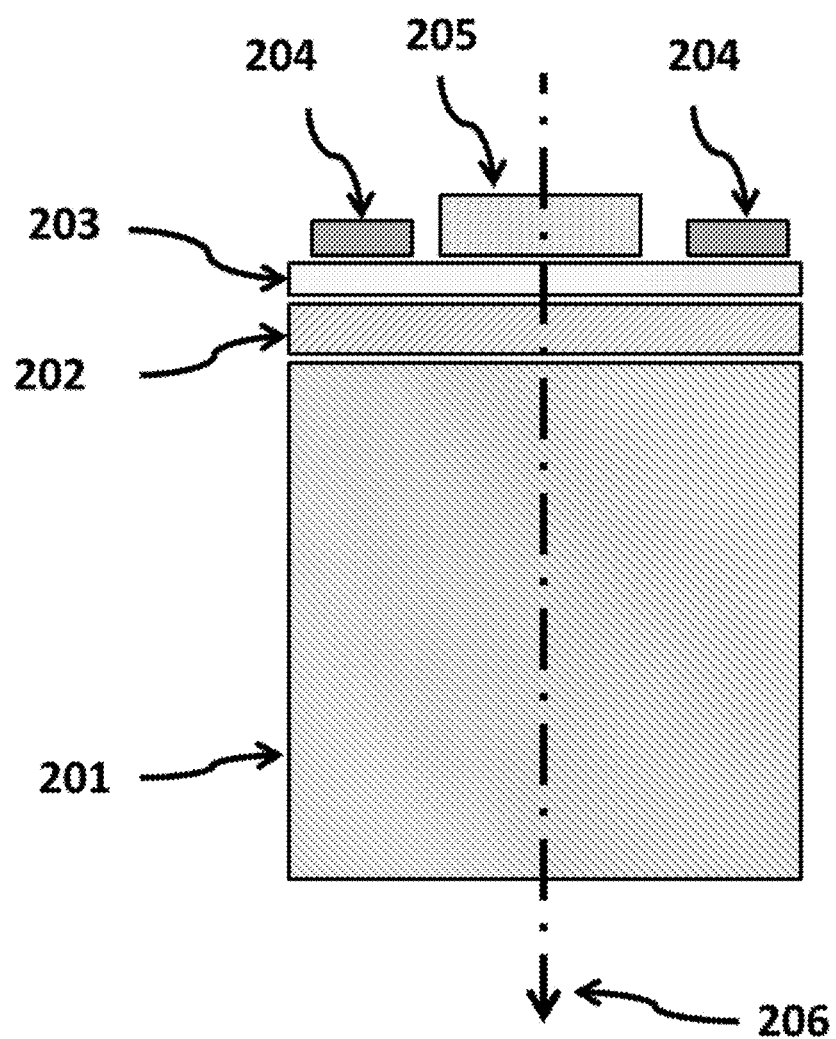
FIG. 2 shows an illustration of one embodiment of the radiation detector and its electronics in a cut-away view to show the inner components.

FIG. 2 illustrates a preferred embodiment of the radiation detector 110 and detector's electronics board 111. The radiation detector, illustrated in FIG. 2, is composed of a scintillation crystal 201 and a surface-mount silicon photomultiplier (SiPM) 202. The scintillation crystal 201 is optically coupled to SiPM 202 either by an optical grease or optical adhesive. To maximize the radiation detection efficiency, the scintillation crystal is selected from common scintillation materials with high density and high effective atomic numbers such as CsI(Tl), GAGG, NaI(Tl), or LYSO. In this embodiment, the complete radiation detection assembly illustrated in FIG. 2 is wrapped with an appropriate light-reflective film and is optically sealed against ambient visible lights.

In one other embodiment, the radiation detector may be made by semiconductor materials such as cadmium zinc telluride (CZT) or cadmium telluride (CdTe). If a semiconductor material is used, it replaces the scintillation crystal 201 and SiPM 202 illustrated in FIG. 2.

SiPM 202 is soldered on one side of a printed circuit board (PCB) 203 and detector electronics components 204 and an inertial measurement unit (IMU) 205 are soldered on the other side of the PCB 203.

The inertial measurement unit (IMU) 205 is equipped with at least a 3-axis accelerometer and a 3-axis gyroscope for tracking the orientation of the radiation probe. In a preferred embodiment, as illustrated in FIG. 2, the accelerometer and gyroscope axis orthogonal to the body of the IMU 205 is aligned with the longitudinal axis 206 of the radiation detector for a more accurate orientation-tracking process. Digital inertial data from the IMU 205 and analog signals from the radiation detector are transmitted to the main electronics board 103 using well insulated wires.

In a preferred embodiment, a microcontroller is used on the main electronics board 103 to process the orientation-tracking data from the IMU 205 in real-time to track the orientation of the radiation probe. The orientation-tracking process is performed in a periodic manner with a period short enough to capture typical angular changes in the probe's orientation.

Before using the radiation probe in a radiation-orientation mapping mode, the user must define a reference orientation in space. Once a reference orientation is defined, any later changes in the orientation of the radiation probe is tracked relative to this reference orientation.

Figure 3:
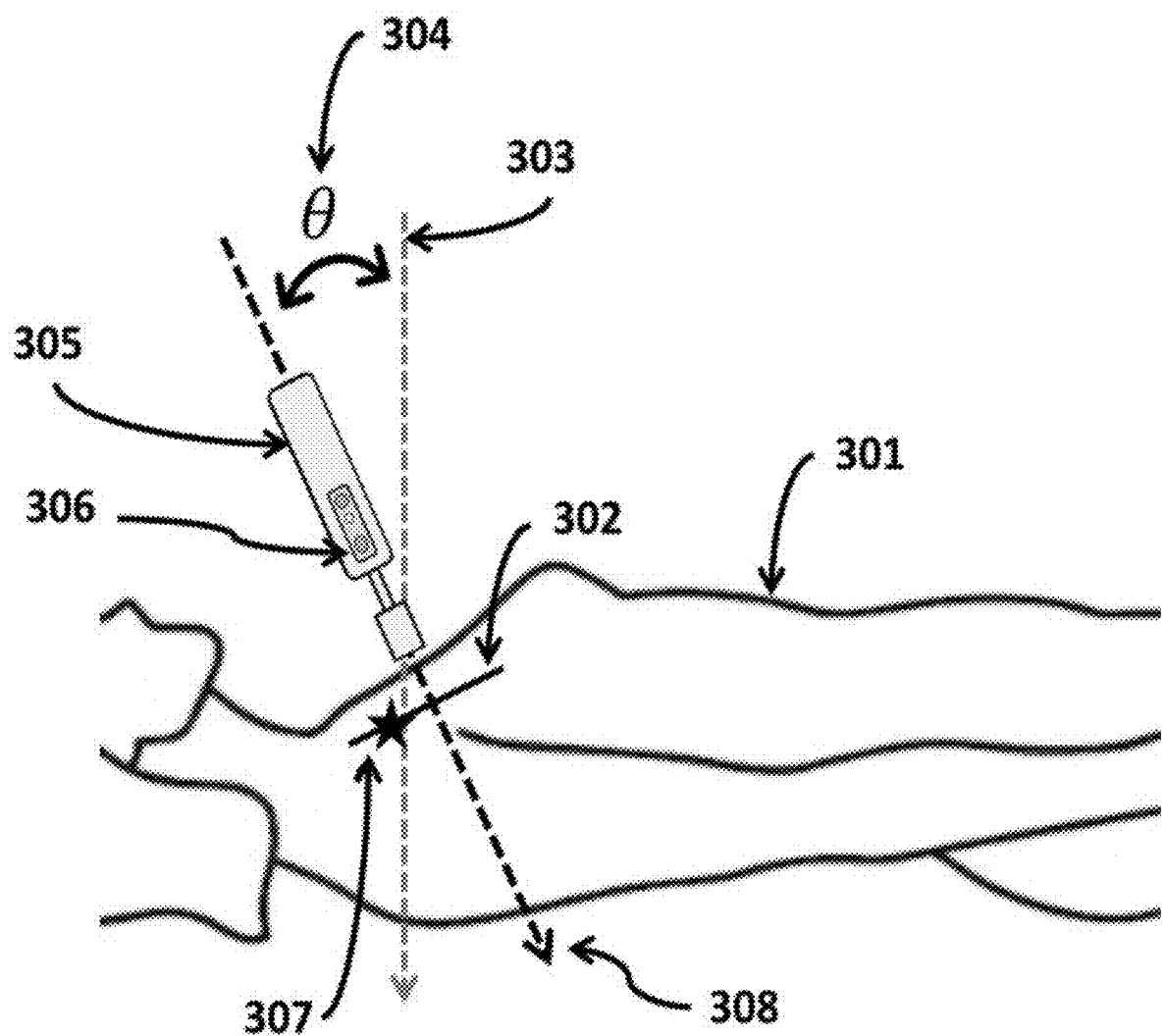
FIG. 3 shows an illustration of using the intraoperative radiation probe relating to the procedure of defining a reference orientation.

FIG. 3 illustrates a simple method in which a reference orientation can be defined by the user. To facilitate the localization of radio-labeled organs in an intraoperative radio-guided surgery, a reference orientation 308 is defined along the probe's orientation toward the patient body 301 whereas the probe's axis approximately crosses the center of a desired target area 302 in the patient body 301. FIG. 3 illustrates a desired target area 302 and a hypothetical radio-labeled organ (star icon) 307 in that area.

Figure 5:
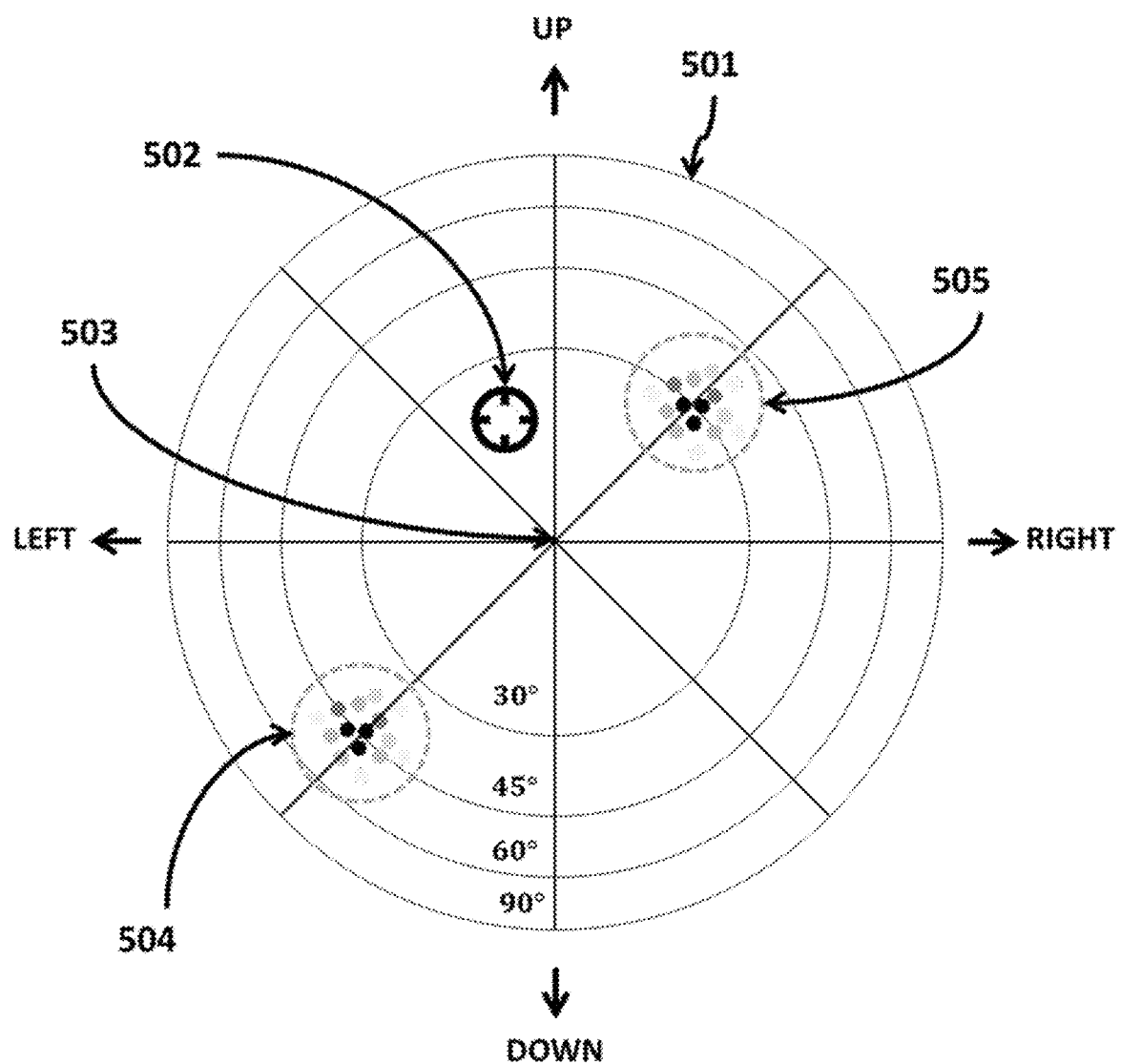
FIG. 5 shows an illustration of a radiation-orientation mapping image relating to the radiation-orientation mapping mode.

To define a reference orientation 308 for the desired target area 302, the user holds the radiation probe 305 toward and perpendicular to the desired target area 302 then pushes and releases the reset button 306. For the system to correctly set the viewing directions (TOP, DOWN, LEFT, and RIGHT) on the radiation-orientation mapping image 501 as illustrated in FIG. 5, the probe's orientation (to be the reference orientation) 308 should not be aligned with the gravity direction 303. Therefore, for defining a new reference orientation, the angel "0" 304 between the probe's orientation 308 and the gravity direction 303 must be at least 5 degrees.

Figure 4:
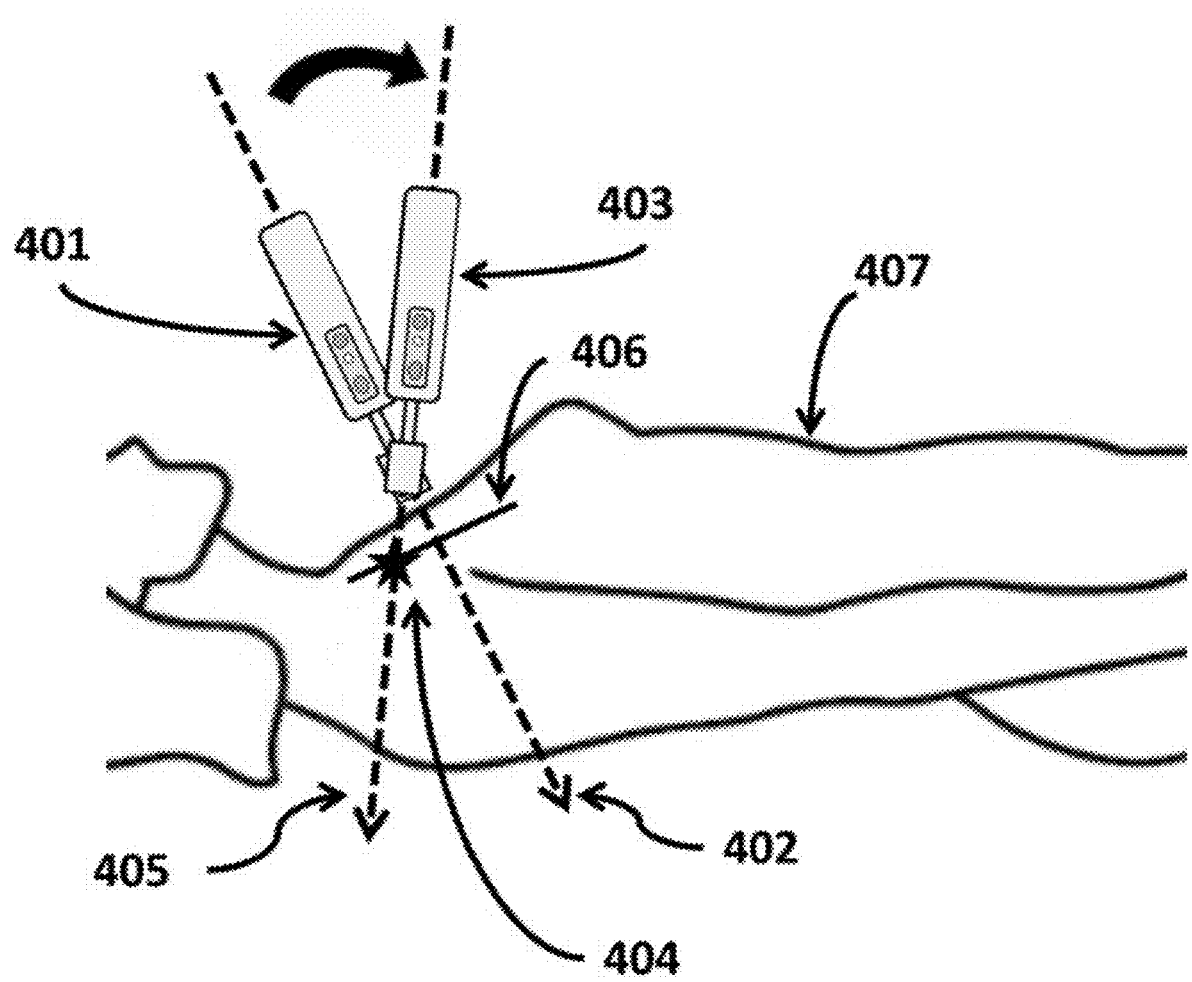
FIG. 4 shows an illustration of using the intraoperative radiation probe relating to the formation of a radiation-orientation mapping image.

By defining a reference orientation, as illustrated in FIG. 3, a new radiation-orientation mapping session is started and the user begins searching the desired target area by changing the probe's orientation and monitoring the radiation-orientation mapping image. In FIG. 4, radiation probe 401 shows the position and orientation of the probe during defining the reference orientation 402 and radiation probe 403 shows the probe with orientation 405 during a search activity afterward. FIG. 4 further illustrates the desired target area 406 and a hypothetical radio-labeled organ (star icon) 404 in that area in the patient body 407.

In a radiation-orientation mapping session, orientation-tracking data along with radiation detection readings are wirelessly transmitted to a personal computer or control unit. The data is then processed in a graphical user interface (GUI) software application running on the personal computer or control unit. The software generates a radiation-orientation mapping image 501, as illustrated in FIG. 5, by fusing orientation-tracking data and radiation detection readings received from the radiation probe.

In a preferred embodiment, to further guide the surgeon, in addition to displaying count-rates and radiation-orientation mapping image, the personal computer or control unit may generate audible signals with pitches proportional to the measured count-rates.

In a preferred embodiment, a radiation-orientation mapping image is a 2D plot with several concentric circles each representing different orientation angles relative to the defined reference orientation within a $2\pi$ steradians solid angle field of view, analogues to a solar zenith/azimuth angle plot. For example, the radiation-orientation mapping image 501 illustrated in FIG. 5 has four concentric circles representing orientation angles at 30, 45, 60, and 90 degrees. The origin point 503 in the radiation-orientation mapping image is always associated with the defined reference orientation. During a radiation-orientation mapping session, the orientation pointer 502 shows the current orientation of the radiation probe relative to the reference orientation (origin point 503) and moves in the radiation-orientation mapping image as the orientation of the radiation probe changes.

As the orientation of the radiation probe changes, mapping marks with different color shades (e.g. from light red to dark red) proportional to the measured instantaneous radiation count-rates or intensity are added to the radiation-orientation mapping image at associated orientations relative to the reference orientation, as illustrated by two detected radioactive hot spots 504 and 505 in FIG. 5.

In one embodiment using a gamma detector with spectroscopy capability to discriminate different radionuclides by measuring their gamma-ray energies, mapping marks with different colors (e.g. red, and blue, and green) associated with different gamma energies are added to the radiation-orientation mapping image to identify and distinguish radioactive hot spots from different radionuclides.

At any time by defining a new reference orientation, the system starts a new radiation-orientation mapping session by bringing the orientation pointer 502 back to the origin point 503 of the radiation-orientation mapping image and erasing all mapping marks from the previous radiation-orientation mapping session.

The application software running on the personal computer or control unit lets the user set a count-rate or intensity threshold level for adding mapping marks to the radiation-orientation mapping image for each radionuclide. Therefore, for each selected radionuclides, the software adds mapping marks to the radiation-orientation mapping image if the corresponding measured radiation intensity at the instantaneous orientation is equal to or above the count-rate or intensity threshold level.

The invention claimed is:

1. An intraoperative radiation probe system for localization of radiation-emitting radionuclides in the body or tissue, the system comprising:
    a handheld radiation probe which comprises: a radiation detector, a tungsten collimator, an inertial measurement unit (IMU), at least one push button mounted on the handheld radiation probe for defining a user-defined reference orientation by a user, and a main electronics board operatively coupled to the at least one push button, the radiation detector and the IMU,
    wherein the main electronics board is configured to process and to determine an energy distribution of incident radiations and an instantaneous orientation data of the handheld radiation probe in space with respect to the user-defined reference orientation; and
    a computer or a control unit with a display screen wirelessly connected to the handheld radiation probe,
    wherein the computer or the control unit is configured to determine an instantaneous radiation count rate from the energy distribution of incident radiations within a predefined energy window, and to generate a two-dimensional radiation-orientation mapping image with concentric circles each representing different orientation angels of the handheld radiation probe with respect to the user-defined reference orientation on the display screen by fusing the instantaneous radiation count rate data and the instantaneous orientation data as processed and determined by the main electronics board of the handheld radiation probe.

2. The intraoperative radiation probe system of claim 1, wherein the radiation detector is responsive to ionizing radiations such as X-rays, gamma rays, beta particles, positron particles, electrons, alpha particles, or neutrons, or a combination of ionizing radiations.

3. The intraoperative radiation probe system of claim 1, wherein the main electronics board is further configured to:
    process radiation-induced electrical signals from the radiation detector to determine the energy distribution of incident radiations detected within a period of time;
    process orientation data from the IMU to determine the instantaneous orientation of the handheld radiation probe in space with respect to the user-defined reference orientation;

register the user-defined reference orientation from the instantaneous orientation of the handheld radiation probe when the user pushes and releases the at least one push button mounted on the handheld radiation probe; and transmit the energy distribution of incident radiations and the instantaneous orientation data to the computer or the control unit periodically and wirelessly.

4. The intraoperative radiation probe system of claim 3, wherein the computer or the control unit is further configured to:

receive the energy distribution of incident radiations and the instantaneous orientation data from the handheld radiation probe periodically and wirelessly;

add mapping marks to the two-dimensional radiation-orientation mapping image periodically with orientation angles corresponding to the instantaneous orientations of the handheld radiation probe with respect to the user-defined reference orientation with varying color shades proportional to the instantaneous radiation count rate if the instantaneous radiation count rate is equal or greater than a user-defined threshold level; and display an orientation pointer on the two-dimensional radiation-orientation mapping image with orientation angles corresponding to the instantaneous orientation of the handheld radiation probe in space with respect to the user-defined reference orientation.

* * * * *